United States Patent
Poli et al.

(10) Patent No.: US 10,188,607 B2
(45) Date of Patent: Jan. 29, 2019

(54) PHARMACEUTICAL FORMULATION OF RACECADOTRIL

(71) Applicant: Rivopharm SA, Manno, Lugano (CH)

(72) Inventors: Piero Poli, Lugano (CH); Alessandro Fiorino, Lugano (CH); Tommaso Roberto Piazzolla, Lugano (CH)

(73) Assignee: Rivopharm SA, Manno, Lugano (CH)

( * ) Notice: Subject to any disclaimer, the term of this patent is extended or adjusted under 35 U.S.C. 154(b) by 0 days.

(21) Appl. No.: 15/549,304

(22) PCT Filed: Dec. 23, 2015

(86) PCT No.: PCT/EP2015/081187
§ 371 (c)(1),
(2) Date: Aug. 7, 2017

(87) PCT Pub. No.: WO2016/128098
PCT Pub. Date: Aug. 18, 2016

(65) Prior Publication Data
US 2018/0028448 A1   Feb. 1, 2018

(30) Foreign Application Priority Data
Feb. 9, 2015   (IT) ............... TO2015A0086

(51) Int. Cl.
| A61K 9/16 | (2006.01) |
| A61K 31/265 | (2006.01) |
| A61K 31/216 | (2006.01) |

(52) U.S. Cl.
CPC .......... *A61K 9/1682* (2013.01); *A61K 9/1623* (2013.01); *A61K 31/216* (2013.01); *A61K 31/265* (2013.01)

(58) Field of Classification Search
CPC .. A61K 31/216; A61K 31/265; A61K 31/353; A61K 31/365; A61K 31/426; A61K 36/38; A61K 36/47; A61K 9/1623; A61K 9/1682; A61K 9/28
See application file for complete search history.

(56) References Cited

U.S. PATENT DOCUMENTS

2009/0186084 A1   7/2009   Schwartz et al.
2010/0273873 A1*  10/2010  Brys ...................... A23G 3/004
                                                        514/474

FOREIGN PATENT DOCUMENTS

| CN | 102166197 A | 8/2011 |
| WO | 01/97803 A1 | 12/2001 |
| WO | WO 0197803 A1 * | 12/2001 | ............. A61K 9/009 |

OTHER PUBLICATIONS

PCT International Search Report and the Written Opinion, Application No. PCT/EP2015/081187 filed Dec. 23, 2015, dated Mar. 10, 2016.

* cited by examiner

*Primary Examiner* — Mark V Stevens
(74) *Attorney, Agent, or Firm* — MacMillan, Sobanski & Todd, LLC

(57) ABSTRACT

The object of the present invention is a pharmaceutical formulation of racecadotril characterized by high bioavailability. In particular, the present invention relates to a method of dry granulating racecadotril in the presence of a hydrophilic excipient and a disintegrant, preferably with a low moisture content; said method being carried out by means of a tablet machine or alternately a roller compacting machine, carrying out the compaction step with a compaction strength of less than 30 kN and equal to or greater than 4 kN, and the step of grinding the slugs and screening so as to obtain a granulate in which not more than 50% by weight of the product has a particle size of less than 90 micron.

19 Claims, 2 Drawing Sheets

PHARMACEUTICAL FORMULATION OF RACECADOTRIL

This is a national stage application filed under 35 U.S.C. § 371 of international application PCT/EP2015/081187, filed under the authority of the Patent Cooperation Treaty on Dec. 23, 2015, published; which claims the benefit of Patent Application No. TO2015A000086, filed on Feb. 9, 2015. The entire disclosures of all the aforementioned applications are expressly incorporated herein by reference for all purposes.

FIELD OF THE INVENTION

The object of the present invention is a pharmaceutical formulation of racecadotril characterized by high bioavailability.

BACKGROUND ART

Racecadotril or acetorphan, (±)-N-[2-[(acetylthio)methyl]-1-oxo-3-phenylpropyl]glycine phenylmethyl ester, is a pediatric and non pediatric antidiarrheal drug having a pure antisecretory mechanism, used to treat acute diarrhea. Chemically, it is a synthetic dipeptide that has the ability to inhibit the peripheral enkephalinase. The antidiarrheal effect is obtained due to a decrease in the secretion of water and intestinal electrolytes, secreted into the lumen of the digestive tract by the myenteric and submucosal plexus.

This substance has been studied since 1993 and patented by the Bioprojet Pharma laboratories; it is marketed in some countries of the world under the names Hidrasec, Tiorfan, Tiorfix.

This drug, however, has the problem of having a low solubility and a very low wettability in water, which negatively affects its bioavailability. In fact, the aqueous solubility and dissolution rate are two key factors that influence the absorption of a drug in the intestinal tract and thereby its bioavailability for oral administration.

The object of the present invention is therefore to provide a pharmaceutical composition of racecadotril having a higher dissolution rate and consequently improved bioavailability.

SUMMARY OF THE INVENTION

The object of the invention is a method for the preparation of a pharmaceutical composition comprising racecadotril as defined in the appended claims.

Further features and advantages of the process according to the invention will be apparent from the following description of preferred embodiments thereof, provided by way of indication and not of limitation.

DETAILED DESCRIPTION OF THE INVENTION

Figure 1:
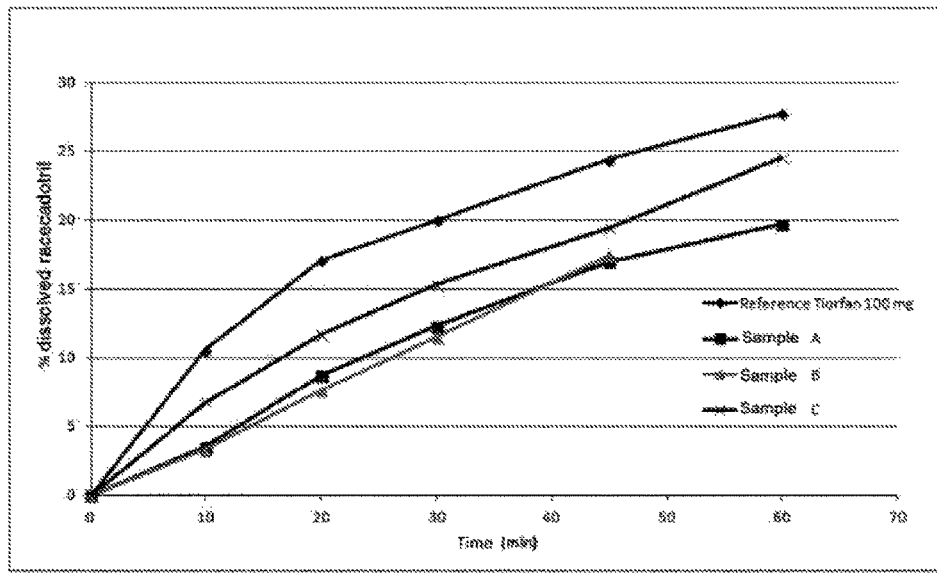
FIG. 1 highlights the influence of the compaction force and, on a second analysis, of the particle size distribution on the dissolution kinetics of the drug in the formulation. The figure shows a dissolution diagram of three different compacted samples obtained from granulates prepared according to the invention, and of a compacted sample obtained from the content of the Tiorfan® 100 mg capsules as a reference, in which the ordinate shows the percentage of drug dissolved, and the abscissa shows the dissolution time.

The present invention relates to a method for obtaining a pharmaceutical composition comprising racecadotril. Such a composition is obtained according to the invention by a method of dry granulation in the presence of a hydrophilic excipient and a disintegrant, preferably having a low moisture content. In a particularly preferred embodiment, the hydrophilic excipient is lactose monohydrate and the disintegrant is pre-gelatinized starch having a low moisture content.

The dry granulation technique is a process by which the pharmaceutical powders are effectively agglomerated so as to form granules even in the absence of a liquid suspension. The formation of granules in the absence of moisture requires the compaction and densification of the powders. In this process, the primary powder particles are aggregated under high pressure.

There are two different dry granulation methods. The first method, known as "slugging", provides for the formation of a large tablet (called a "slug") in a tablet press, while the second consists in passing the powder under two compacting rollers that form a compact ribbon. In both cases, the "slugs" or the ribbon obtained are subjected to a grinding and consequent calibration technique in order to obtain a granulate characterized by a suitable particle size distribution.

It has been shown that, by using the dry granulation technique, three parameters are important in determining shorter dissolution times. The first is the compaction strength to which the intra-granular mixture is subjected for obtaining the slugs or the ribbon, the second is the particle size of the granulate obtained after grinding and calibration of the slugs, the third is the type of disintegrant used in the formulation.

It has been shown that in order to obtain a granulate having a dissolution kinetics comparable to that of the product Tiorfan® taken as a reference, a compaction strength of the intra-granular mixture of less than 30 kN and equal to or greater than 4 kN must be applied. In particular, such a strength must be preferably in the range between 4 and 15 kN. Moreover, following grinding and calibrating the slugs, a granulate must be obtained in which no more than 50% by weight of product has a particle size of less than 90 micron.

Moreover, it has been shown that in order to obtain a formulation having a dissolution kinetics comparable to that of the reference product Tiorfan® 100 mg and achieve an optimization of the process, it is necessary to use a starch-based disintegrant in the formulation, preferably pre-gelatinized starch with a low moisture content. A description of this excipient can be found in "Handbook of Pharmaceutical Excipients", ed. Raymond C. Rowe, Paul J. Sheskey, Walter G. Cook and Marian E. Fenton, 2012.

This excipient is particularly suitable both for the dry granulation process (performed by means of a "slugging" or roller compaction) technique and for the formulation of poorly water-soluble drugs, due to its properties as:

Diluent: it helps to improve the flow properties of powder guaranteeing a uniform level of filling of the dies during the process; the ideal conditions are thus created for the production of even slugs/ribbon and, in the last analysis, of homogeneous granules in terms of density.

Disintegrant: in contact with an aqueous dissolution medium, the pre-gelatinized starch swells and triggers the disintegration mechanism of the granules, through which it allows the release of the active ingredient which is therefore more rapidly available to be solvated by the dissolution medium. The preferred choice of a pre-gelatinized starch with a low moisture content enhances the disintegration mechanism, increasing the kinetics of passage of the active ingredient into solution.

Non-stick: it significantly decreases the adhesion of the powders to the mechanical elements of the production plant during the slugging step, allowing an optimization of the process.

The method according to the invention comprises the following steps:

a) mixing an amount of racecadotril with a diluent and pharmaceutically acceptable excipients obtaining an intra-granular mixture;

b) subjecting the mixture of step a) to a compaction according to the slugging technology, with a compaction strength greater than or equal to 4 kN and less than 30 kN, so as to obtain "slugs" or ribbon;

c) grinding and calibrating the slugs/ribbon obtained in step b) so as to obtain a granulate in which not more than 50% by weight of product has a particle size of less than 90 micron;

d) adding extra-granular excipients to the granulate of step c), thus obtaining the end mixture comprising racecadotril.

The method of the invention may comprise a further step of dividing the end mixture comprising racecadotril in suitable capsules for oral administration and release into the gastro-intestinal tract.

Step a)

The diluent is preferably lactose monohydrate. The diluent may be used in amounts in the range between 30% and 50% by weight with respect to racecadotril.

Pharmaceutically acceptable excipients that may be selected for the granulate of the invention are a lubricant and/or a glidant and/or a disintegrant. Other excipients such as binders, disintegrants and so on may also be used.

The lubricant is preferably comprised in the granulate in weight amounts between 5% and 10% with respect to racecadotril.

The glidant is preferably comprised in the mixture in weight amounts between 0.5% and 3% with respect to racecadotril.

The disintegrant is preferably comprised in the mixture in weight amounts between 50% and 70% with respect to racecadotril.

A preferred lubricant is magnesium stearate.

A preferred glidant is colloidal silica.

A preferred disintegrant is pre-gelatinized starch, preferably having a low moisture content.

Step b)

The "slugging" technology is a conventional technique. For example, a description of this technology can be found in Handbook of Pharmaceutical Granulation Technology, ed. Dilip M. Parikh, 1997.

In preferred embodiments, the compaction strength to which the intra-granular mixture is subjected is in the range between 4 and 20 kN, preferably between 4 and 15 kN.

A rotary type tablet machine is preferably used and the slugs formed preferably have a weight of about 1 g. Alternatively to the rotary type tablet machine, a roller compacting machine may be used.

Step c)

After grinding of the slugs and subsequent calibration, a granulate is obtained having, as said, not more than 50% by weight of product with particle size of less than 90 microns.

In preferred embodiments, between 30% and 80% of the granulate has a particle size ranging between 90 and 710 micron, and not more than 20% by weight of the product has a particle size equal to or greater than 710 micron.

Step d)

The extra-granular excipients are preferably a lubricant and/or a diluent and/or a disintegrant. The disintegrant is added in this step only if it is absent in the mixture of step a).

The disintegrant, when used, is present in weight amounts between 50% and 70% with respect to racecadotril. A preferred disintegrant is pre-gelatinized starch, preferably having a low moisture content.

The extra-granular lubricant is preferably used in weight amounts between 1% and 3% with respect to racecadotril. A preferred lubricant is magnesium stearate.

Examples of formulations according to the invention are shown hereinafter (table 1).

TABLE 1 examples of formulation of the invention.

| Ingredients | EXAMPLE 1 mg/capsule | EXAMPLE 2 mg/capsule | EXAMPLE 3 mg/capsule | EXAMPLE 4 mg/capsule |
|---|---|---|---|---|
| Intra-granular phase | | | | |
| Racecadotril | 100.00 | 100.00 | 100.00 | 100.00 |
| Lactose monohydrate | 41.00 | 41.00 | 41.00 | 41.00 |
| Colloidal silica | 2.00 | 2.00 | 2.00 | 2.00 |
| Magnesium stearate | 11.00 | 9.00 | 11.00 | 9.00 |
| Pre-gelatinized starch | 59.00 | / | / | 61.00 |
| Extra-granular phase | | | | |
| Pre-gelatinized starch | / | 61.00 | 59.00 | / |
| Magnesium stearate | 2.00 | 2.00 | 2.00 | 2.00 |
| TOT | 215.00 | 215.00 | 215.00 | 215.00 |

Three different types of granulates were prepared according to the invention by means of slugging technology, starting from a percentage composition shown in table 2. The slugs were prepared by working with a compaction strength of 15±2 kN (sample A), 20±2 kN (sample B) and 10±2 kN (sample C), respectively, and using standard pre-gelatinized starch as disintegrant.

TABLE 2 examples of slugs prepared with different compaction forces.

| | A | B | C |
|---|---|---|---|
| | \multicolumn{3}{c}{Compaction strength applied} | | |
| Ingredients | 15 ± 2 kN | 20 ± 2 kN | 10 ± 2 kN |
| Racecadotril | | 46.51% | |
| Lactose monohydrate | | 19.07% | |
| Pre-gelatinized starch | | 27.44% | |
| Colloidal silica | | 0.93% | |
| Magnesium stearate | | 6.05% | |
| TOT | | 100.00% | |

Thereafter, dissolution tests were carried out in order to evaluate the influence of the compaction force and particle size distribution (table 3) on the dissolution rate of the drug in the formulation.

Table 3: particle size distribution of the granulates produced by applying different compaction forces.

| Sieve | Sample A 15 kN | Sample B 20 kN | Sample C 10 kN |
|---|---|---|---|
| >710 μm | 8.49% | 10.47% | 4.50% |
| <500 μm | 73.11% | 69.77% | 82.00% |

To prevent that the dissolution rate of capsule jeopardizing the dissolution kinetics of the active ingredient, the final mixture comprising the racecadotril granulate was enriched with a super disintegrant (crospovidone, 60 mg/dosage unit) and tablets were prepared with the mixture thus obtained using a round bi-convex punch (7 mm diameter, 9 mm bending radius) at a very low compaction strength (1.5±0.1 kN), thus obtaining soft, porous and rapidly disintegrating tablets. The compaction parameters used and the features of the tablets obtained are shown in table 4.

Table 4: compaction parameters and physical characteristics of the racecadotil tablets produced for the dissolution test.

| Compaction strength | 1.5 ± 0.5 kN |
|---|---|
| Average weight | ~280 mg |
| Thickness | 7.5 ± 0.1 mm |
| Disintegration time | <30" |

The tablet thus obtained was inserted into a support consisting of a helical shaped metal wire (like a spring), which allows keeping the tablet submerged in water (otherwise, the tablet would float due to its low density) but without preventing the wettability of the tablet by the dissolution means.

The dissolution test results are shown in FIG. 1. As can be seen from the diagram, lower compaction forces and thereby finer particle size distributions correspond to faster dissolution kinetics. While a decreasing compaction force applied results in an increased dissolution rate, the dissolution profiles related to the slugs obtained according to the invention are not comparable to what found for the reference drug.

Thereafter, two granulates were prepared according to the invention by means of slugging technology, starting from a percentage composition shown in table 2. The slugs were prepared using a compaction force of 10±2 KN and using the following in the formulation, respectively:

SAMPLE C: standard pre-gelatinized starch (manufacturer's moisture content specification: 0-14%)

SAMPLE D: pre-gelatinized starch with a low moisture content (manufacturer's moisture content specification: 0-7%).

Dissolution tests were then carried out in order to evaluate the influence of the disintegrant grade on the dissolution rate of the drug in the formulation.

In order to prevent the dissolution rate of capsule influencing the dissolution kinetics of the active ingredient, the steps were as described above on page 13.

Figure 2:
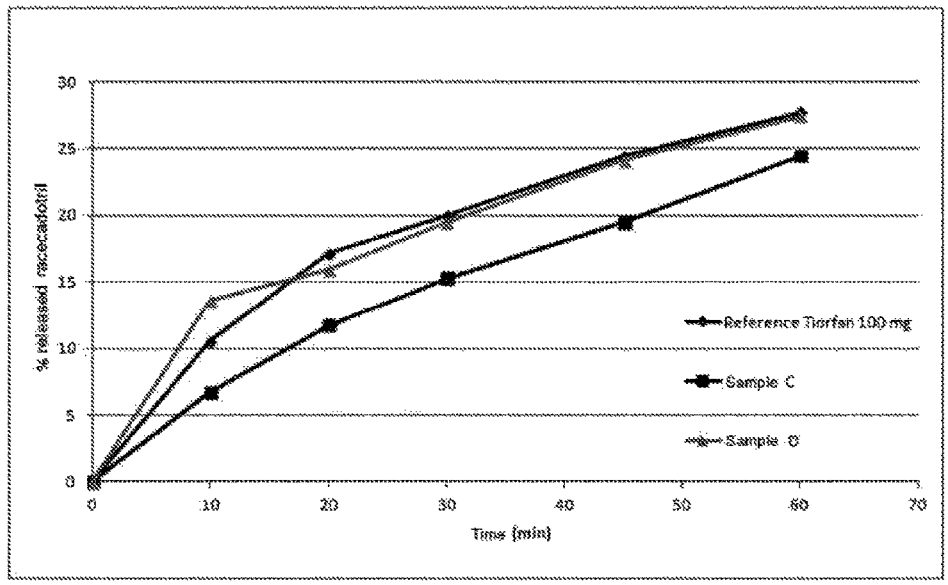
FIG. 2 highlights the influence of the grade of disintegrant on the dissolution kinetics of the drug in the formulation; the figure shows a dissolution diagram of two different compacted samples obtained from granulates prepared according to the invention, compared with the dissolution profile of compacted samples obtained from the content of the Tiorfan® 100 mg capsules as a reference, in which the ordinate shows the percentage of drug dissolved, and the abscissa shows the dissolution time.

The dissolution test results are shown in FIG. 2. As can be seen from the diagram, with equal compaction force, the use of pre-gelatinized starch with a low moisture content allows obtaining faster and similar dissolution kinetics than those found for the reference Tiorfan 100 mg.

Thereafter, a comparison dissolution test was carried out between the reference product Tiorfan® 100 mg capsules and two different granulates obtained according to the invention, divided into capsules:

sample 1 obtained by applying a compaction force of 10 kN and using pre-gelatinized starch with a low moisture content as disintegrant;

sample 2 obtained by applying a compaction force of 30 kN and using pre-gelatinized starch with a low moisture content as disintegrant.

Sample 1 has the following particle size distribution:

TABLE 5 particle size distribution of Sample 1

| Sieve μm | % retained |
|---|---|
| Bottom | 28.8% |
| 90 | 26.7% |
| 250 | 25.8% |
| 500 | 12.1% |
| 710 | 6.6% |

Figure 3:
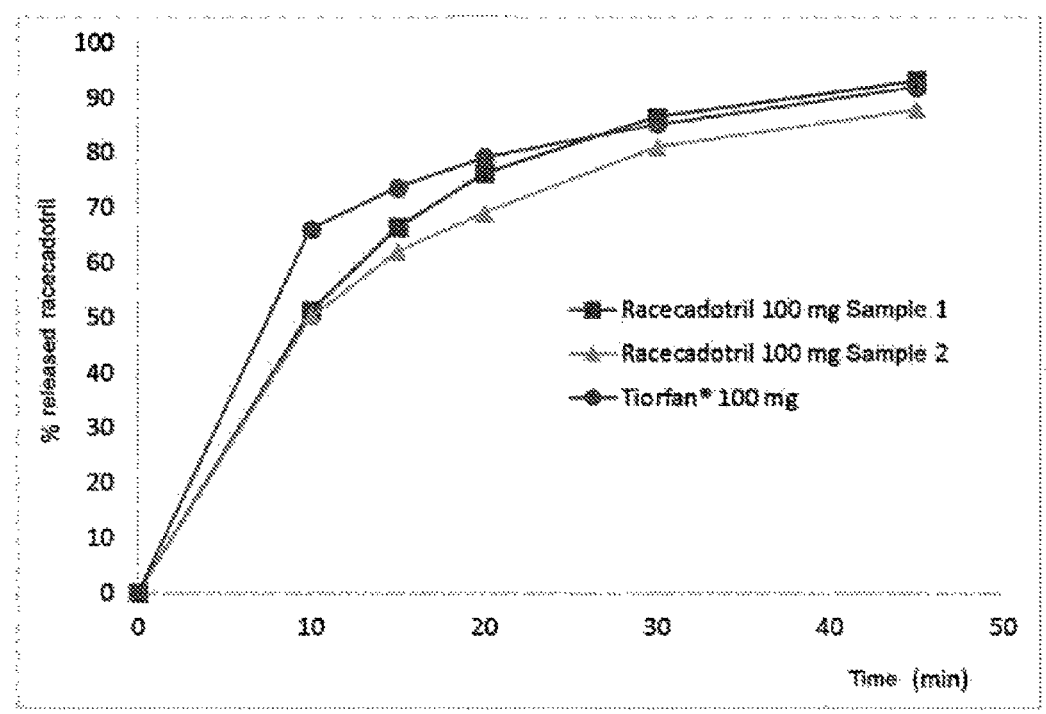
FIG. 3 shows a dissolution diagram of two different samples of capsules containing 100 mg of active granulate according to the invention and of Tiorfan® 100 mg capsules as a reference, in which the ordinate shows the percentage of drug dissolved, and the abscissa shows the dissolution time.

The dissolution test results are shown in FIG. 3 and table 6. As can be seen, sample 1 shows a dissolution profile similar to that of the reference compound Tiorfan®, while the dissolution profile of sample 2 is unsatisfactory.

TABLE 6 percentage of racecadotril released from the samples tested in 900 mL of purified water plus 2.0% sodium lauryl sulfate, 37.0 ± 0.5° C., 150 rpm, apparatus II (USP).

| Time (min) | Racecadotril 100 mg Sample 1 % released | Racecadotril 100 mg Sample 2 % released | Tiorfan ® 100 mg % released |
|---|---|---|---|
| 10 | 51.2 ± 3.4 | 50.2 ± 2.3 | 66.1 ± 2.2 |
| 15 | 66.4 ± 2.4 | 61.9 ± 1.2 | 73.6 ± 3.6 |
| 20 | 76.2 ± 2.0 | 69.0 ± 1.2 | 79.1 ± 3.2 |
| 30 | 86.5 ± 3.2 | 80.9 ± 1.6 | 85.1 ± 2.9 |
| 45 | 93.1 ± 2.3 | 87.9 ± 1.3 | 91.9 ± 3.3 |

The following values of f2 were also calculated:
  i) between Tiorfan® and sample 2=47
  ii) between Tiorfan® and sample 1=53.

These values were calculated according to the guidelines "On The Investigation Of Bioequivalence CPMP/EWP/QWP/1401/98 Rev 1".

These values show that the similarity in vitro (f2≥50) can only be achieved with sample 1 obtained by compaction at 10 kN. Sample 1 was also bioequivalent in vivo compared to the reference Tiorfan® 100 mg capsules (table 7).

TABLE 7 pharmacokinetic parameters derived from the bioequivalence study between Tiorfan® 100 mg capsules (reference) and Sample 1.

| Parameter | CV % intra-subject | Geometric LS mean Sample 1 | Geometric LS mean Reference Tiorfan | Ratio (%) Sample 1/ Reference | 90% confidence limits (%) Lower limit | 90% confidence limits (%) Upper limit |
|---|---|---|---|---|---|---|
| $C_{max}$ | 35.9 | 164.83 | 173.29 | 95.12 | 87.02 | 103.97 |
| $AUC_T$ | 19.1 | 263.99 | 272.73 | 96.80 | 92.21 | 101.61 |

Unit of measure: ng/mL for $C_{max}$ and h/mL for $AUC_T$

Based on the results obtained, Racecadotril 100 mg capsules were also subsequently produced replicating the qualitative and quantitative composition of Sample 1 and using a roller compactor in the dry granulation step. In particular, a granulate was prepared having physical and chemical features equivalent to those described for sample 1. The granulate obtained was then mixed with magnesium stearate and the mixture thus prepared divided into capsules.

The Racecadotril 100 mg capsules obtained by dry granulation process using a roller compactor were characterized in terms of dissolution kinetics. The results are shown in table 8.

Table 8: percentage of racecadotril released from the samples tested in 900 mL of purified water plus 2.0% sodium lauryl sulfate, 37.0±0.5° C., 150 rpm, apparatus II (USP).

| Time (min) | Racecadotril 100 mg Sample 1 Dry granulation with slugging machine % released | Racecadotril 100 mg Sample 1 Granulation with roller compactor % released | Tiorfan® 100 mg % released |
|---|---|---|---|
| 10 | 51.2 ± 3.4 | 57.4 ± 3.7 | 66.1 ± 2.2 |
| 15 | 66.4 ± 2.4 | 69.3 ± 4.6 | 73.6 ± 3.6 |
| 20 | 76.2 ± 2.0 | 76.2 ± 3.8 | 79.1 ± 3.2 |
| 30 | 86.5 ± 3.2 | 86.1 ± 2.7 | 85.1 ± 2.9 |
| 45 | 93.1 ± 2.3 | 93.7 ± 2.2 | 91.9 ± 3.3 |

The following values of f2 were also calculated:
i) Between Tiorfan® and sample 1 (dry granulation with slugging machine)=53
ii) between Tiorfan® and sample 1 (dry granulation with roller compactor)=64
iii) between sample 1 (dry granulation with slugging machine) and sample 1 (dry granulation with roller compactor)=72.

These values were calculated according to the guidelines "On The Investigation Of Bioequivalence CPMP/EWP/QWP/1401/98 Rev 1". These values show the similarities in vitro (f2≥50) between the different samples tested irrespective of the dry granulation technique used. The method of production of the Racecadotril granulate is therefore independent of the type of equipment used (tablet press machine or roller compactor).

* * *

From the above it is clear that the method according to the invention is able to produce a racecadotril granulate bioequivalent to the reference commercial product Tiorfan® and has the advantage of being a simple and cost-effective method. In fact, working with a lower compaction strength and with a larger particle size than the known formulations allows a reduction of costs (less wear of the punch/compaction roller and lower use of energy) and process times. The production method also allows obtaining a product that is stable over time (table 8).

TABLE 8 stability of sample 1 stored at 25° C.-60% relative humidity and 40° C.-75% relative humidity in Alu/PVC-PVDC blister.

25° C.-60% RH

| Test | Specifications | Unit | 0 month | 3 months | 6 months | 9 months | 12 months | 18 months | 24 months |
|---|---|---|---|---|---|---|---|---|---|
| Appearance | Hard gelatine opaque yellow-opaque yellow capsules, size 2. Capsules contain white or almost white powder | | Complies | Complies | Complies | Complies | Complies | Complies | Complies |
| Identification | Positive (UPLC) | | Positive | Positive | Positive | Positive | Positive | Positive | Positive |
| Dissolution test | ≥75% after 45 minutes | % | 92.7 | 95.0 | 101.2 | 97.7 | 98.0 | 94.9 | 96.8 |
| Assay | 95.0%-105.0% | % | 100.5 | 99.5 | 99.3 | 99.9 | 100.2 | 99.1 | 101.4 |
| Related substances | Impurity C ≤ 0.2% | % | <0.1 | <0.1 | <0.1 | <0.1 | <0.1 | <0.1 | <0.1 |
| | Each unknown impurity ≤ 0.2% | % | <0.1 | <0.1 | <0.1 | <0.1 | <0.1 | <0.1 | <0.1 |
| | Total (known + unknown) ≤ 1.0% | % | <0.1 | <0.1 | <0.1 | <0.1 | <0.1 | <0.1 | <0.1 |
| Water content (KF) | Analyze and record | % | 3.2 | 4.0 | 4.2 | 4.3 | 4.3 | 4.5 | 4.5 |

40° C.-75% RH

| Test | Specifications | Unit | 0 month | 1 month | 2 months | 3 months | 6 months |
|---|---|---|---|---|---|---|---|
| Appearance | Hard gelatine opaque yellow-opaque yellow capsules, size 2. Capsules contain white or almost white powder | | Complies | Complies | Complies | Complies | Complies |

TABLE 8-continued stability of sample 1 stored at 25° C.-60% relative humidity and 40° C.-75% relative humidity in Alu/PVC-PVDC blister.

| | | | | | | | |
|---|---|---|---|---|---|---|---|
| Identification | Positive (UPEC) | | Positive | Positive | Positive | Positive | Positive |
| Dissolution test | ≥75% after 45 minutes | % | 92.7 | np | np | 95.4 | 92.7 |
| Assay | 95.0%-105.0% | % | 100.5 | 101.0 | 98.6 | 100.1 | 99.3 |
| | Impurity C ≤ 0.2% | % | <0.1 | <0.1 | <0.1 | <0.1 | <0.1 |
| Related substances | Each unknown impurity ≤ 0.2% | % | <0.1 | <0.1 | <0.1 | <0.1 | rrt 0.33: 0.10<br>rrt 0.97: 0.10<br>rrt: 1.45: 0.10<br>rrt 1.47: 0.11 |
| | Total (known + unknown) ≤ 1.0% | % | <0.1 | <0.1 | <0.1 | <0.1 | 0.41 |
| Water content (KF) | Analyze and record | % | 3.2 | np | np | 5.0 | 5.3 |

The invention claimed is:

1. A method of dry granulating racecadotril in the presence of a diluent and a disintegrant, the diluent being lactose monohydrate, said method being carried out by means of a dry granulation technique by operating
    a compaction step with a compaction strength of less than 30 kN and equal to or greater than 4 kN, and
    a step of grinding and calibration of the slugs and/or ribbon so as to obtain a granulate in which not more than 50% by weight of the product has a particle size of less than 90 microns.

2. The method according to claim 1, wherein the disintegrant has a low moisture content.

3. The method according to claim 1, comprising a further step of encapsulation of the end mixture comprising racecadotril in capsules for oral administration and release into the gastro-intestinal tract.

4. The method according to claim 1, the diluent is used in amounts from 30% to 50% by weight with respect to racecadotril.

5. The method according to claim 1, wherein the pharmaceutical excipient is a lubricant and/or glidant,
    wherein the lubricant, if present, is contained in the mixture in a weight amount from 5% to 10% with respect to racecadotril,
    wherein the glidant, if present, is contained in the mixture in a weight amount from 0.5% to 3% with respect to racecadotril, and
    wherein the disintegrant is contained in the mixture in a weight amount from 50% to 70% with respect to racecadotril.

6. The method according to claim 5, wherein the lubricant is magnesium stearate, and/or the glidant is colloidal silica, and/or the disintegrant is pre-gelatinized starch.

7. The method according to claim 1, wherein the compaction strength is from 4 to 20 kN.

8. The method according to claim 1, wherein from 30% to 80% by weight of the granulate has a particle size from 90 to 710 microns, and not more than 20% by weight of the granulate has a particle size equal to or greater than 710 microns.

9. A method of dry granulating racecadotril in the presence of a diluent and a disintegrant, the diluent being lactose monohydrate, comprising the following steps:
    a) mixing an amount of racecadotril with the diluent, and optionally a disintegrant, and pharmaceutically acceptable excipients obtaining an intra-granular mixture;
    b) subjecting the mixture of step a) to a compaction step with a compaction strength greater than or equal to 4 kN and less than 30 kN, so as to obtain slugs and/or a compacted product;
    c) grinding and calibrating the slugs and/or the compacted product of step b) so as to obtain a granulate in which not more than 50% by weight of product has a particle size of less than 90 microns and;
    d) adding extra-granular excipients to the granulate of step c), thus, obtaining the end mixture comprising racecadotril.

10. The method according to claim 9, wherein in step d) the extra-granular excipients are a lubricant and/or a diluent.

11. The method according to claim 10, wherein in step d) the extragranular excipients further include a disintegrant if a disintegrant is absent in the intra-granular mixture of step a).

12. The method according to claim 11, wherein the disintegrant is present in a weight amount from 50% to 70% by weight with respect to racecadotril, said disintegrant being pre-gelatinized starch.

13. The method according to claim 11, wherein the extra-granular lubricant is used in a weight amount from 1% to 3% with respect to racecadotril, said lubricant comprising magnesium stearate.

14. The method according to claim 9, wherein step a) lactose monohydrate is used in an amount from 30% to 50% by weight with respect to racecadotril.

15. The method according to claim 9, wherein the mixture of step a) further contains a lubricant and/or glidant,
    wherein the lubricant, if present, is contained in the mixture in a weight amount from 5% to 10% with respect to racecadotril,
    wherein the glidant, if present, is contained in the mixture in a weight amount from 0.5% to 3% with respect to racecadotril, and
    wherein the disintegrant, if present, is contained in the mixture in a weight amount from 50% to 70% with respect to racecadotril.

16. The method according to claim 9, wherein step b) the compaction strength to which the mixture of step a) is subjected to is from 4 to 20 kN.

17. The method according to claim 9, wherein from 30% to 80% by weight of the granulate has a particle size from 90 to 710 microns, and not more than 20% by weight of the granulate has a particle size equal to or greater than 710 microns.

18. The method according to claim 9, comprising a further step of encapsulation of the end mixture comprising racecadotril in capsules for oral administration and release into the gastro-intestinal tract.

19. The method according to claim 15, wherein the lubricant is magnesium stearate, and/or the glidant is colloidal silica, and/or the disintegrant is pre-gelatinized starch.

* * * * *